United States Patent [19]

Arnold

[11] Plant 4,253

[45] May 16, 1978

[54] PLANT OF THE FERN FAMILY

[76] Inventor: Elizabeth R. Arnold, 3846 Loretto Rd., Jacksonville, Fla. 32223

[21] Appl. No.: 798,607

[22] Filed: May 19, 1977

[51] Int. Cl.[2] ..... A01H 9/00

[52] U.S. Cl. ..... Plt./88

[58] Field of Search ..... Plt./88

*Primary Examiner*—Robert E. Bagwill

*Attorney, Agent, or Firm*—George H. Baldwin; Arthur G. Yeager

[57] ABSTRACT

A new and distinct variety (cultivar) of fern plant of the group known commercially as "Boston ferns" has been discovered and propagated. The new cultivar originated as a vegetative variant ("bud sport") of a plant of *Nephrolepis exaltata* cv. Verona, and is distinguished from its parent and other cultivars of "Boston ferns" by fronds that have shorter, more numerous and crowded divisions which grow entangled with one another to produce thick matted blades, and by pinnules that have laminae which are very small, variable in shapes but predominately narrowly linear, irregularly pinnatifid or forked.

5 Drawing Figures

1

This disclosure relates to a population of cultivated fern plants believed to represent a new and distinct type of "Boston fern", and which has been named *Nephrolepis exaltata* cv. Frizzie Lizzie by the discoverer.

There are many types of "Boston fern" that have been given cultivar names and known today in the foliage plant market and still others no longer are recognized to be of commercial value. These all are members of a variety known to science as *Nephrolepis exaltata* var. *Bostonensis* and all are considered to be vegetative variations and descendants of an original fern in the Boston area. These cultivars differ in their growth forms and in the forms of their leaves and leaflets. The original variety was and still is a rather coarse fern with leaves once-pinnately compound. Today there are dwarf races as well as ones with leaves 3 and 4 times compound and some with minute leaflets.

Interest in the new cultivar mainly centers in its repeatedly dissected leaves with short divisions and small variable laminae and that grow into a dense "fluff" of entangled adjacent leaves. The whole plant becomes a matted misty green dome that hides its container and makes an interesting house-plant.

Recognized in April, 1973 growing from a bud on the stolon of cv. Verona, the new shoot appeared in sharp contrast with other parts of that plant. Separated from its parent the new plantlet was grown and propagated in the same greenhouse and has remained stable and unlike the parent cultivar through 10 generations of vegetative propagations.

Currently several dozen plants of the new cultivar are uniform and easily distinguishable from other types of ferns known to the discoverer. From ferns which generally resemble it such as cv. Smithii, cv. Fantasia it differs by:

a. Leaves pendant at an earlier age and tending to continue to be bent abaxially.

b. Divisions of the blade crowded into thicker, denser "fluff" entangled with adjacent leaflets and leaves.

c. Laminae of the young leaf resembling those of cv. Verona but on older leaves predominantly narrowly linear, irregularly pinnatifid or dichotomously branched.

My new variety is shown in the accompanying color photographic drawings wherein:

2

Figure 1:
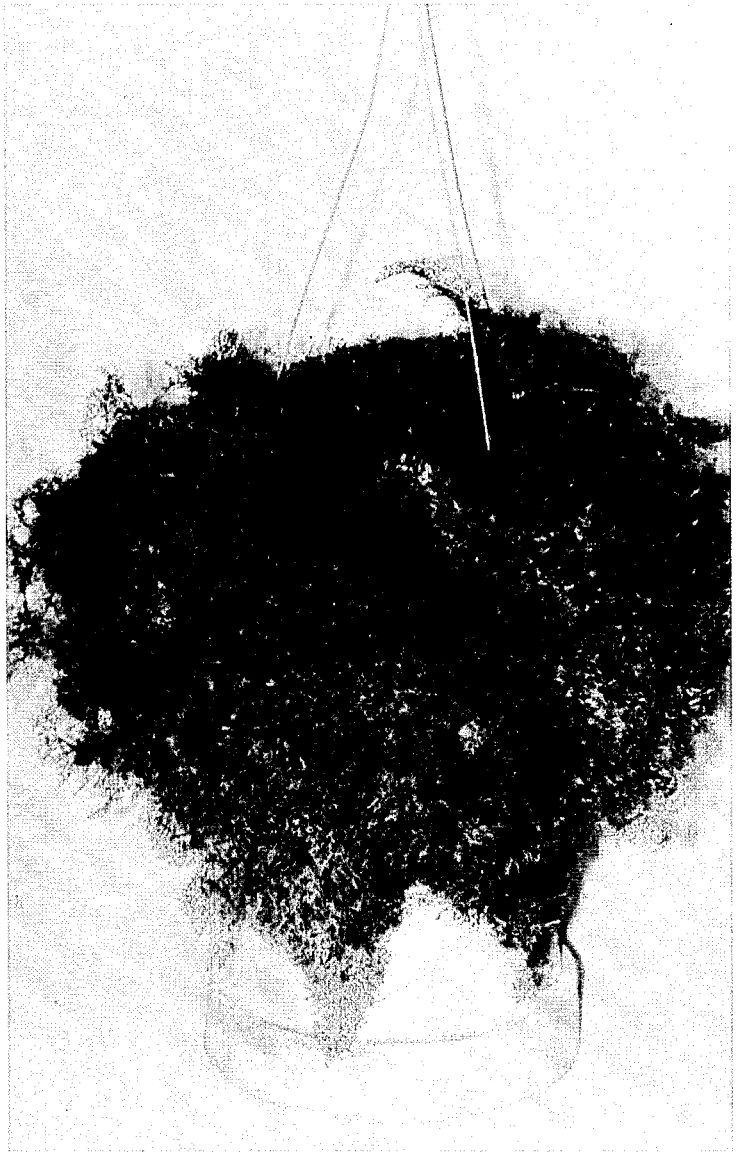
FIG. 1 is a side view of a typical specimen growing in a hanging basket and showing tips of a few nearly erect young fronds appearing at the top and a mass of non-erect and generally downwardly bent leaves of which the oldest hang close to and completely hide the basket, the basket being positioned on a 10 inch diameter clay pot.
Figure 2:
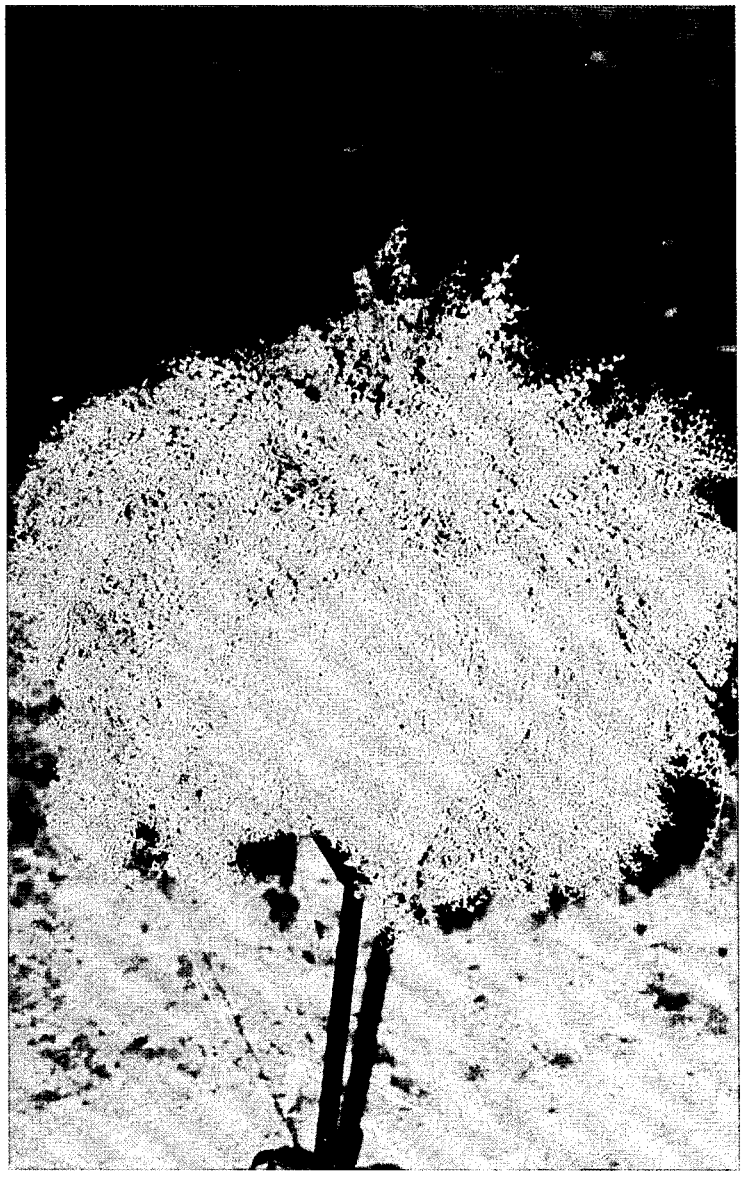
FIG. 2 is a similar view of a specimen having a typical moderate yellow-green color of a specimen according to the invention.
Figure 3:
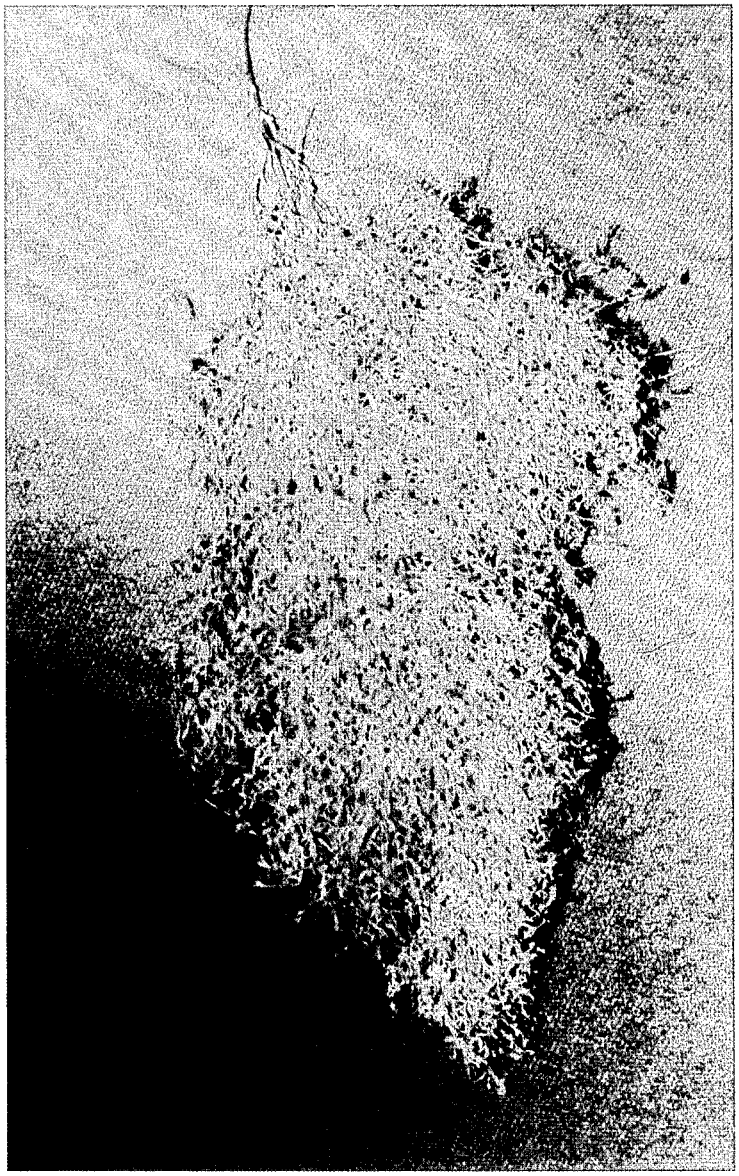
Figure 4:
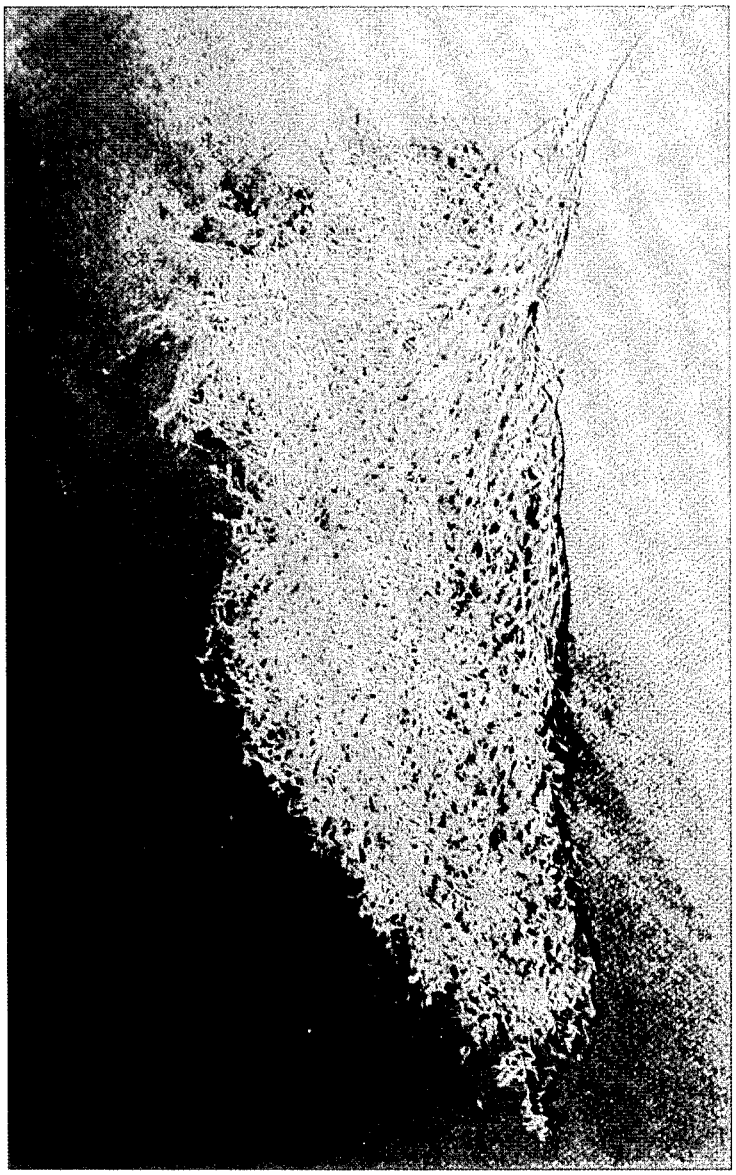
Figure 5:
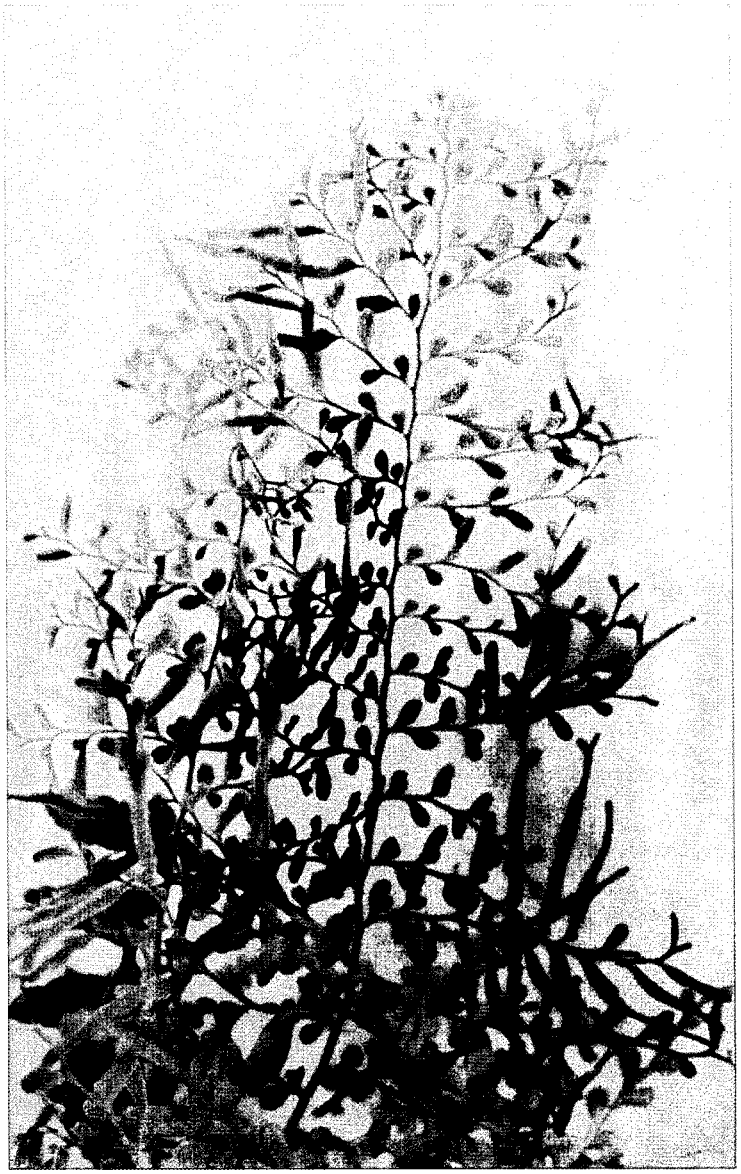

FIGS. 3 and 4 are a top or adaxial view and a side or edge view, respectively, of the same single frond showing the delicate and entangled divisions of the leaf blade and of the small ultimate pinnules, and the fluffy matted growth pattern of the repeatedly branched segments of the leaf, the whole frond shown being approximately 20 cm. in length; and FIG. 5 is a macro-photographic print of small ultimate divisions of a terminal portion of a frond, approximately 4 cm. overall, showing details of typical pinnae and pinnules of a specimen of the variety.

DETAILED DESCRIPTION

The following is a description of a plant of the new fern cultivar grown under usual glass-house care in light approximately 35% of full sunlight at Woodside Fernery, Jacksonville, Fla.

Name: *Nephrolepis exaltata* cv. Frizzy Lizzy, E. Arnold.

Parentage: *Nephrolepis exaltata* cv. Verona by vegetative variation ("sport").

Classification: Willis, J. C. A Dictionary of Flowering Plants and Ferns, 8th ed., 1973, Cambridge Univ. Press.

*Division.*—Pteridophyta. Class — Fillicopsida. Sub-class — Filicidae. Order — Davalliales. Family — Oleandraceae. Genus — Nephrolepis. Species — *exaltata.*

GENERAL FORM

Terrestrial, shade tolerant, herbaceous fern plant that is sexually sterile.

Stems: As in other Boston ferns the stems are of two types. The short rooted leaf-bearing stems produce the clumps of leaves. These are connected with one another by the horizontal leafless stolons.

(A) Leaf-bearing stems are erect, partly subterranean, cylindric in shape and usually about 1 cm. long and 1–5 mm. in diameter. Their surfaces are nearly covered by minute scales, crowded leaf bases and adventitious roots. Internally the vascular tissues have a dictyostelic arrangement surrounded by parenchyma of about equal amounts. Leaves are produced acropetally for an undetermined length of time as older leaves die below.

(B) Stolons are pale green or straw-colored, leafless, flexible, and about 1 mm. in diameter. Growing from between leaf bases these special branches extend horizontally mainly above ground in all directions from the parent leafy stem. The surfaces of the stolons contain numerous lanceolate scales that are one cell thick, 1–4 mm. long and usually less than 1 mm. wide. Internally the central core of protostelic vascular tissues is surrounded by a narrow cylinder of parenchyma that contains few chloroplasts. At intervals of about 3–6 cm., buds may appear on the stolon. From these buds are produced new leaf-bearing stems with their leaves and with adventitious roots anchored in the substrate. These buds on the stolons and similar ones produced rarely on leaves and roots serve as the only natural means of propagating the plant.

LEAVES (A) General — A single leaf, or frond, of the new fern consists of a slender stalk, (stipe) and a compound blade made up of a main axis (rachis) to which are attached the compound pinnae that consist of primary and secondary axes and their terminal flattened laminae. As in other Boston ferns the blades of the leaves are the principal visible parts of the plants because they overgrow the stems and lower parts of the leaves. Color of the plant is largely that of its leaves, and usually is moderate yellow-green Munsell color hue 5 GY 5/6, but darker shades of green appear after application of nitrogenous fertilizers or when the plants are kept heavily shaded. Because growing points occur at the ends of the rachis and all of its pinnae a leaf is capable of growing very large. However, an optimal size for the new fern leaves is about 40 cm. in length and 6 cm. in width at the middle of the blade. At this size under ordinary greenhouse care some of the older pinnae tend to become yellow and crowded and preferably may be pruned away.

(B) Stipe. The stalk of the frond is slightly flat on its adaxial side, bears numerous scales like those of the stolons, and grows to about 2 mm. in diameter and 4 cm. in length. In young leaves the stipe is slender yet rigid enough to hold the blade nearly erect and has the same color as the blade. As the blade is enlarged the stipe becomes bent downward and its color changes to yellow-green, or brownish but it remains flexible.

(C) Rachis. This is the main axis of the blade from its lowest pinna to its growing apex. It is a continuation of the stipe and resembles it in shape and color. Scales on the rachis are fewer toward its apex and short hairs are more numerous. Along both sides of the rachis the pinnae are attached alternately and gradually closer together toward the apex. Color of the rachis is the same as that of the adjacent pinnae.

(D) Pinnae. Younger and smaller pinnae are often only once compound, but pinnae that are 10 cm. or more long usually are 3 pinnatifid. The pinnae and their segments grow at an angle toward the apex of the blade, and at an angle adaxial to the plane of the blade. This tends to establish thickness and fluff to the blade as a whole. The primary and secondary axes of the pinnae are essentially branches from the rachis and are similar to it in appearance. The closeness of the segments of the pinnae and their angle of growth cause them to entangle with other segments of the same or adjacent pinnae or even adjacent fronds. Generally the secondary axes of pinnae gradate into the pinnules or into their short stalked segments and have similar coloration and dermal hairs.

(E) Pinnules. These are the primary divisions of the pinnae. Sizes and forms of the pinnules and shapes of their laminae constitute distinctive features of this new fern. In the original type of Boston fern the pinnae are not divided, and hence the term pinnule does not apply. In the new cultivar the pinnae generally are divided sometimes once, usually twice, rarely three times and terminate in flat segments, laminae, that contain veins. Most Boston ferns produce a few foliar segments that resemble pinnae of the original variety, and must be pruned out to keep a uniform appearance. Such "reversion" segments are rare in the new cultivar.

Larger laminae are about 5mm. wide and up to 12 mm. long. The shorter ones are obovate or fan-shaped, while other are lanceolate or nearly linear. Their margins are crenate or shallowly lobed. Venation of the larger segments is asymetrically pinnate and open (not netted). The single main vein is non-median, nearer the basiscopic margin, and its pinnately arranged branches usually are once forked and each veinlet ends in an obvious enlargement close to the margin of the lamina.

Smallest segments of pinnules frequently are only 1 mm. wide and up to 20 mm. long and supplied by a single median vein. Some of these narrow linear laminae are forked or irregularly lobed, in which case each fork or lobe is supplied by a branch vein ending.

Laminae of intermediate sizes are mostly obovate or fan-shaped and have crenate margins. Their largest dimension generally is 2–8 mm. and their veinlets are evenly distributed, forked, and without a midrib.

Regardless of size, all pinnules have epidermal hairs distributed along the margins of their laminae and on the undersides of veins. Each hair is composed of a tier of 4–6 cells and terminated by a single globose cell that is larger than the diameter of other cells of the hair. Similar hairs occur on other parts of the frond where they may be accompanied by scales.

Tissue between veins varies in thickness from papery thin and translucent in smaller pinnules to thicker and opaque in larger ones. Color hue in pinnules varies with thickness of the laminae so their number and small sizes may cause the lighter color of the new cultivar as compared with many other Boston ferns.

ROOTS

These ferns do not have primary root systems. The adventitious roots grow out from the leafy stems and from buds that arise on stolons and elsewhere. The roots are long, slender and sparsely branched. They differ from stolons mainly by their dark brown color, and by their growth into the substrate rather than parallel to its surface.

Roots of the new cultivar are numerous but they seem restricted to the upper few centimeters of soil. By contrast other Boston ferns grown in the same conditions have deeper root systems.

I claim:

1. The new and distinct plant variety of Boston fern substantially as herein described and characterized by a growth habit which provides specimens with repeatedly dissected leaves with short divisions and small variable pinnules and that appears as a dense fluffy dome-shaped mass of entangled leaves, and that, in comparison to *Nephrolepis exaltata* cv. Smithii and cv. Fantasia, has leaves which become pendant at an earlier age and which tend to continue to be bent abaxially, has divisions of the blade which so crowd into each other and into adjacent leaflets and leaves as to form a thicker, denser and fluffier mass, and has pinnules with laminae predominantly more narrowly linear, irregularly pinnatifid or dichotomously branched, the overall color of said specimens being substantially moderate yellow green.

* * * * *